US006838433B2

(12) United States Patent
Serlupi-Crescenzi et al.

(10) Patent No.: US 6,838,433 B2
(45) Date of Patent: Jan. 4, 2005

(54) IL-6 ANTAGONIST PEPTIDES

(75) Inventors: Ottaviano Serlupi-Crescenzi, Rome (IT); Alessandro Bressan, Rome (IT); Linda Della Pietra, Rome (IT); Anna Rita Pezzotti, Rome (IT)

(73) Assignee: Applied Research Systems ARS Holding N.V., Curacao (NL)

( * ) Notice: Subject to any disclaimer, the term of this patent is extended or adjusted under 35 U.S.C. 154(b) by 54 days.

(21) Appl. No.: 10/357,479

(22) Filed: Feb. 4, 2003

(65) Prior Publication Data

US 2003/0186876 A1 Oct. 2, 2003

Related U.S. Application Data

(62) Division of application No. 09/715,923, filed on Nov. 20, 2000, now Pat. No. 6,599,875, which is a continuation of application No. PCT/EP99/03421, filed on May 18, 1998.

(30) Foreign Application Priority Data

May 18, 1998 (EP) ............................................. 98108997

(51) Int. Cl.[7] ........................ A61K 38/00; A61K 38/08; C07K 14/00; C07K 14/52
(52) U.S. Cl. ............................... 514/2; 514/13; 514/14; 514/15; 514/16; 530/300; 530/350; 530/326; 530/327; 530/328; 424/85.2
(58) Field of Search ............................... 514/2, 13, 14, 514/15, 16; 530/300, 350, 326, 327, 328; 424/85.2

(56) References Cited

U.S. PATENT DOCUMENTS 5,981,219 A * 11/1999 Flugge et al. ............... 435/69.1

6,004,813 A * 12/1999 Serupi-Crescenzi et al. .................... 435/375
6,599,875 B1 * 7/2003 Serlupi-Crescenzi et al. .. 514/2

FOREIGN PATENT DOCUMENTS

WO WO 9713781 A2 * 4/1997
WO WO 9748728 A1 * 12/1997
WO WO 9960013 A2 * 11/1999

OTHER PUBLICATIONS

Dittrich et al., Identification of a Region within the Cytoplasmic Domain of the Interleukin–6 (IL–6) Signal Transducer gp130 Important for Ligand–induced Endocytosis of the IL–6 Receptor, J. Biol. Chem. 269, 19014–19020 (1994).*
Narazaki et al., Soluble Forms of the Interleukin–6 Signal–Transducing Receptor Component gp130 in Human Serum Processing a Potential to Inhibit Signals Through membrane–Anchored gp130, Blood 82 (4) 1120–1126 (1993).*
Murakami et al. Critical Cytoplasmic Region of the Interleukin 6 Signal Transducer gp130 Is conserved in the Cytokine Receptor Family, Proc. natl. Acad. Sci. USA 88, 11349–11353 (1991).*

* cited by examiner

Primary Examiner—Jon Weber
Assistant Examiner—Chih-Min Kam
(74) Attorney, Agent, or Firm—Browdy and Neimark (57) ABSTRACT

The present invention relates to IL-6 antagonist peptides, isolatable from a peptide library through the two-hybrids system by their ability to bind to the intracellular domain of gp130 and containing at least 5 amino acids. In particular, such peptides comprise the amino acid sequence SEQ ID NO: 6, as well as salts, functional derivatives, precursors and analogs thereof. The present invention also provides the peptides in substantially purified form, in order to be suitable for use in pharmaceutical compositions as active ingredient in pathologies that require IL-6 activity inhibition.

7 Claims, 5 Drawing Sheets

Figure1

Vectors used in the screening for gp130-binding peptides.

I group:

| Clone A | | | | | | | I | G | L | S | S | E | V | G | R | G | D | NO:3 |
|---|---|---|---|---|---|---|---|---|---|---|---|---|---|---|---|---|---|---|
| Clone B | A | G | P | V | K | A | M | A | V | V | R | V | G | R | R | S | | 4 |
| Clone C | | | | | | | M | G | G | L | T | R | V | G | | | | 2 |

II group:

| Clone D | | | | T | E | S | P | H | Q | N | N | H | R | A | E | T | S | M | 5 |
|---|---|---|---|---|---|---|---|---|---|---|---|---|---|---|---|---|---|---|---|
| Clone E | W | G | D | N | E | W | W | R | S | E | P | H | K | M | E | L | | | 6 |

III group:

| Clone F | A | G | W | K | P | L | A | C | R | W | T | R | S | G | I | A | 7 |
|---|---|---|---|---|---|---|---|---|---|---|---|---|---|---|---|---|---|

IV group:

| Clone G | N | C | K | A | V | E | G | L | V | P | L | E | L | V | S | G | 8 |
|---|---|---|---|---|---|---|---|---|---|---|---|---|---|---|---|---|---|

V group:

| Clone H | R | L | R | A | 13 |
|---|---|---|---|---|---|

FIG. 4
Peptides

| Clone D | | | | | T | E | S | P | H | Q | N | N | H | R | A | E | T | S | M |
|---|---|---|---|---|---|---|---|---|---|---|---|---|---|---|---|---|---|---|---|
| Clone E, E₁ | W | G | D | N | E | W | W | R | S | E | P | H | K | M | E | L | | | |
| JAK1 (367-383 a.a.) | E | S | V | V | S | I | N | K | Q | D | N | K | K | M | E | L | | | |

| Clone E, E₁ | W | G | D | N | E | W | W | R | S | E | P | H | K | M | E | L |
|---|---|---|---|---|---|---|---|---|---|---|---|---|---|---|---|---|
| BTK (245-261 a.a.) | E | S | N | L | P | W | W | R | A | R | D | K | N | G | Q | E |
| TEC (208-224 a.a.) | K | N | D | V | H | W | W | R | A | R | D | K | Y | G | N | E |
| ITK (212-228 a.a.) | S | S | E | I | H | W | W | R | V | Q | D | R | N | G | H | E |

| Clone C | M | G | G | L | T | R | V | G |
|---|---|---|---|---|---|---|---|---|
| TYK 2 (24-32 a.a.) | M | G | G | L | K | V | L | L |

FIG. 6

Relevant homologies

US 6,838,433 B2

1

IL-6 ANTAGONIST PEPTIDES

CROSS-REFERENCE TO RELATED APPLICATIONS

The is a division of parent application Ser. No. 09/715,923, filed Nov. 20, 2000, now U.S. Pat. No. 6,599,875, which is continuation of PCT/EP99/03421, filed May 18, 1998, which is herein incorporated entirely by reference.

FIELD OF THE INVENTION

The present invention relates to IL-6 antagonist peptides, isolatable from a peptide library through the two-hybrids system by their ability to bind to the intracellular domain of gp130 and containing at least 5 amino acids. In particular, such peptides comprise an amino acid sequence, which is selected from the group consisting of: SEQ ID NO: 1, SEQ ID NO: 3, SEQ ID NO: 4, SEQ ID NO: 5, SEQ ID NO: 6, SEQ ID NO: 7, SEQ ID NO: 8, as well as salts, functional derivatives, precursors and analogs thereof.

Another object of the present invention is to provide the peptide in substantially purified form, in order to be suitable for use in pharmaceutical compositions, as active ingredient, in pathologies that require IL-6 activity inhibition.

BACKGROUND OF THE INVENTION

The Two Hybrid System (THS) is a method that uses transcriptional activity as a system to detect protein-protein interactions. A gene fusion is constructed to encode the DNA-binding domain of the yeast transcription factor GAL4 as a hybrid with any protein 'X' (usually a defined mammalian protein being the "bait" binding target). An additional gene fusion construct will encode the transcription activation domain of GAL4 fused to any protein 'Y' (usually a library of diverse proteins, the "fish") (Fields et al., 1994). Whenever an X-Y interaction does occur, it will bring the activation domain close to sites on the DNA recognized by the GAL4 DNA-binding domain, therefore resulting in the expression of a flanking reporter gene regulated by these DNA sites. The reporter genes commonly used include: 1) lacZ, which produces blue colonies on plates or filters containing X-Gal; and 2) His3, a yeast gene involved in histidine biosynthesis, required for growth of host yeast cells.

Recently, Fields and his team have used the THS for screening a library of random peptides, instead of a cDNA library, in order to find peptides capable of binding to the retinoblastoma protein (Rb) (Yang et al., 1995).

The receptor system for Interleukin-6 (IL-6) is composed of two distinct receptor "subunits" designated gp80 and gp130 (see Hirano et al., 1994).

The IL-6 type cytokines elicit their signal through receptors that share the gp130 protein. Upon ligand binding gp130 homo- or heterodimerizes with the LIF and OSM receptor, thereby activating associated JAK tyrosine kinases. The JAKs phosphorylate the signal transducer (gp130) and latent transcription factors of the STAT family (Signal Transducer and Activator of Transcription), like STAT1 and STAT3 in the case of IL-6. STAT factors dimerize, translocate to the nucleus and bind to enhancer elements of IL-6 responsive genes (Lüttiken et al., 1993).

Deletion analysis of the intracellular domain of gp130 has defined short stretches of amino acids known as box1 and box2 sufficient to impart both mitogenic activity and binding of JAK proteins (Vanderkuur et al., 1994): these activities were also observed when the binding sites of STATs were deleted. Therefore two functions can be ascribed to JAK kinases: 1) activation of STAT-mediated gene expression; 2) activation of STAT-independent mitogenic activity at least in some hematopoietic cells.

Additional kinases are known to associate with to the intracellular portion of gp130, such as Hck, Fes, Btk and Tec (Matsuda et al., 1995). However these interactions have not been elucidated at the molecular level. Moreover, Tanner et al. have demonstrated that the box1 domain of cytokine receptors is required but not sufficient for interaction with JAK kinases and have suggested that the box1 sequences cooperate with other cytoplasmic domain sequences to effect JAK kinase association (Tanner et al., 1995). Even the molecular counterpart on JAK kinases of box1 and box2 has not been defined.

Synthetic peptides that inhibit IL-6 activity have been described in the International Patent Application WO 97/13781 (YEDA), which relates to peptides derived from the gp80 protein.

DESCRIPTION OF THE INVENTION

As a target in the THS, we have analyzed the intracellular portion of the human IL-6 receptor (gp130-ICD). This THS screening should therefore identify candidate peptides which are able to directly interact with gp130-ICD in a phosphorylation-independent manner. Phosphorylation independent-interactions with gp130-ICD are known to occur in the transduction of the signal triggered by IL-6 type cytokines. gp130-ICD interacting counterparts of this type include protein kinases of the JAK family (Darnell et al., 1994).

Therefore, the main object of the present invention is an IL-6 antagonist peptide, isolatable from a peptide library through the two-hybrids system by their ability to bind to the intracellular domain of gp130 and containing at least 5 amino acids. According to a preferred embodiment of the invention, such peptides contain up to 30 amino acids, more preferably 5–20, most preferably 8–16.

According to the present invention the "bait" ("X") used in the THS screening is the intracellular domain (ICD) of the gp130 protein. Such domain corresponds to the region from amino acid at position 642 to amino acid at position 918 (Yamasaki K. et al., 1988) of the IL6-R (gp130). The "fish" in the THS screening is a library of random peptides. Such library can be any commercial library or can be produced "in-house" by known methods.

False positives arising from the above screening may be eliminated as described in the literature (Bartel et al., 1993).

According to a further preferred embodiment, such peptides comprise an amino acid sequence, which is selected from the group consisting of: SEQ ID NO; 1, SEQ ID NO: 3, SEQ ID NO: 4, SEQ ID NO:5, SEQ ID NO: 6, SEQ ID NO: 7, SEQ ID NO: 8, as well as salts, functional derivatives, precursors and analogs thereof.

When, in SEQ ID NO: 1, $Xaa^3$ is Gly and $Xaa^4$ is Leu, the peptide of the invention comprises the amino acid sequence of SEQ ID NO: 2.

"Analogs", as used in the present application, means those peptides, in which one or more of the amino acids in the above sequences are changed without substantially affecting the IL-6 antagonist activity. In particular, preferred changes for analogs in accordance with the present invention are what are known as "conservative" substitutions. Conservative amino acid substitutions include amino acids replacements with synonymous amino acids within the same group, which have sufficiently similar physiochemical properties that substitution between members of the group will preserve the biological function of the molecule, Grantham, *Science* Vol. 185, pp. 862–864 (1974).

The synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Gln, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE III

Most Preferred Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

The term "salts" herein refers to both salts of carboxyl groups and to acid addition salts of amino groups of the peptides of the invention or analogs thereof. Salts of a carboxyl group may be formed by means known in the art and include inorganic salts, for example, sodium, calcium, ammonium ferric or zinc salts, and the like, and salts with organic bases as those formed, for example, with amines, such as triethanolamine, arginine or lysine, piperidine, procaine and the like. Acid salts include, for example, salts with mineral acids such as, for example, hydrochloric acid or sulphuric acid, and salts with organic acids such as, for example, acetic acid or oxalic acid. Of course, any such salts must have substantially similar activity to the peptides of the invention or its analogs.

The definition "functional derivatives" as herein used refers to derivatives which can be prepared from the functional groups present on the lateral chains of the amino acid moieties or on the terminal N- or C-groups according to known methods and are comprised in the invention when they are pharmaceutically acceptable i.e. when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alkanoyl- or aroyl-groups.

The "precursors" are compounds which are converted into the peptides of the invention in the human or animal body.

The "IL-6 antagonist activity" means ability to inhibit IL-6 activity by antagonizing the binding of IL-6 to its receptor and/or by interfering with the function of the receptor system which transduces, intracellularly, molecular signals leading to the gene activation in IL-6-dependent cells, such as, for example, myeloma cells. Therefore, such activity may be measured by any of the assays known in the art. Such assays include proliferation of murine plasmacytoma T1165 cells, growth inhibition of mouse M1 myeloid leukemia cells, or production of acute phase proteins from hepatoma cells.

The peptides of the invention may be prepared by any well known procedure in the art, such as solid phase synthesis or liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their α-amino groups and side chain functional groups protected with appropriate protective groups are condensed one by one in order from the C-terminus to the N-terminus, and one where the amino acids bound to the resin or the protective group of the α-amino groups of the peptides are released, the peptide chain is thus extended in this manner. Solid phase synthesis methods are largely classified by the tBoc method and the Fmoc method, depending on the type of protective group used.

Typically used protective groups include tboc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and $Cl_2$-Bzl (2,6-dichlorobenzyl) for the amino groups; $NO_2$ (nitro) and Pmc (2,2,5,7,8-pentamethylchromane-6-sulphonyl) for the guanidino groups); and tBu (t-butyl) for the hydroxyl groups).

After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

The crude peptide thus obtained is then subjected to purification. Purification is carried out by any one of the methods known for this purpose, i.e. any conventional procedure involving extraction, precipitation, chromatography, electrophoresis, or the like. For example, HLC (high performance liquid chromatography) can be used. The elution can be carried using a water-acetonitrile-based solvent commonly employed for protein purification.

Another object of the present invention is, therefore, to provide the peptide in substantially purified form, in order to be suitable for use in pharmaceutical compositions, as active ingredient, in pathologies that require IL-6 activity inhibition.

Pathologies in which the new peptides according to the invention are advantageously used for prophylactic, therapeutic or diagnostic uses include haematological diseases, immune system diseases, bone diseases, tumours and auto-immune diseases, as well as therapy for transplantation including solid organ and cellular transplants.

Specific examples of the above categories include the following diseases: chronic lymphocytic leukemia (CLL), plasmacytoma/multiple myeloma, Castleman's disease (CD), osteoporosis, psoriasis, multiple sclerosis, lupus erithematosus, diabetes, rheumatoid arthritis as well as anaemia and wasting in chronic diseases.

Further objects and advantages of the invention will be evident in the following description.

An embodiment of the invention is the administration of a pharmacologically active amount of the peptide of the invention to subjects at risk of developing pathologies requiring IL-6 activity inhibition or to subjects already showing such pathologies.

Any route of administration compatible with the active principle can be used, but particularly preferred is the parenteral administration because it permits to have, in short times, systemic effects.

The dose of peptide to be administered depends on the basis of the medical prescriptions according to age, weight and the individual response of the patient.

The pharmaceutical composition for parenteral use can be prepared in injectable form comprising the active principle and a suitable vehicle. Vehicles for the parenteral administration are well known in the art and comprise, for example, water, saline solution and physiologic buffers. The vehicle can contain smaller amounts of excipients in order to maintain the solution stability and isotonicity.

The preparation of the cited solutions can be carried out according to the ordinary modalities.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Screening of the Peptide Library

Figure 1:
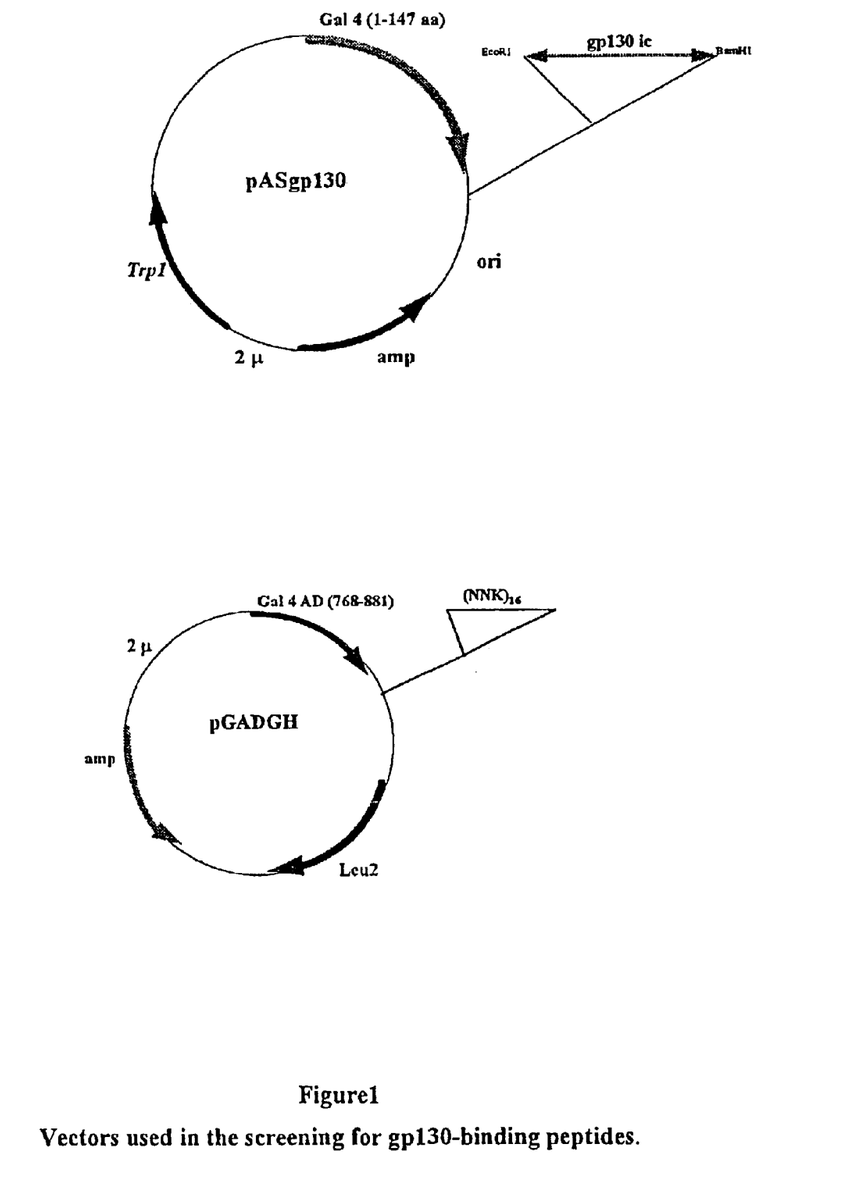
FIG. 1: Vectors used in the screening for gp130-binding peptides. The plasmid pASgp130 encodes GAL4 DNA-binding domain (residues 1–147 a.a.) fused to gp130-ICD; the plasmid, pGADGH encodes a library of random 16-mer peptides $(NNK)_{16}$ (SEQ. ID. NO: 19) fused to the GAL4 activation domain (residues 768–881 a.a.).

A 16-mer random peptides library has been screened with the Two-Hybrid System (THS). The yeast GAL4 activation domain (AD) coding sequence was ligated in frame to a random library of synthetic oligonucleotides which coding for the peptides. The vector used, pGADGH, is a centromeric plasmid carrying the ADH1 promoter and the yeast Leu2 gene as a selectable marker (FIG. 1). The random peptide library is estimated to contain about $10^7$ independent clones (see Material and Methods).

RT-PCR was performed in HepG2 cells, in order to isolate the intracellular portion of human gp130. The corresponding cDNA was cloned in frame with the yeast GAL4 binding domain (BD) coding sequence in plasmid pAS2-1. This is a centromeric plasmid carrying the ADH1 promoter and the yeast TRP1 gene as a selectable marker.

Figure 2:
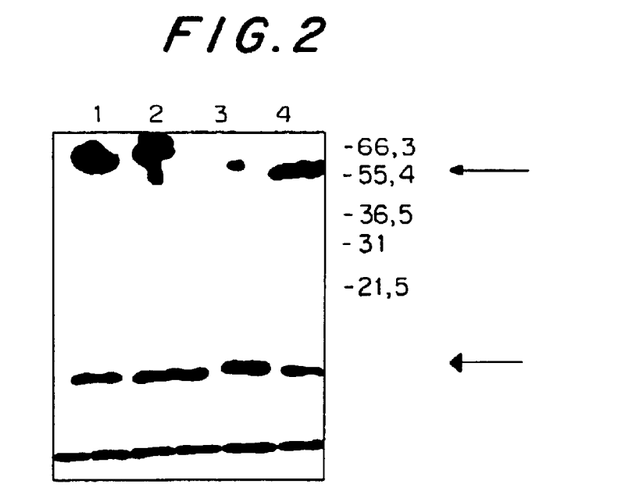
FIG. 2: Western blotting of yeast extracts. CG-1945 (lanes 1 and 2) was transformed with pAS2-1, coding for GAL4BD (lane 3) or with pASgp130, coding for gp130-GAL4BD (lane 4). Protein extracts were separated on a 15% acrylamide-SDS gel and analyzed by a cheriluminescence detection system. Molecular weights are indicated (kilodaltons). The black arrow denotes gp130-GAL4BD; the grey arrow denotes GAL4BD.

The expression of fusion protein has been verified by Western blotting (FIG. 2).

In our experiments, we used the yeast strain CG-1945, which carries two reporter genes, lac Z and His3 (Estojak et al., 1995).

We used 60 μg of the peptide library for each transformation of the recipient yeast cells previously transformed with the plasmid coding for the fusion protein gp130ic-GAL4BD. In order to find the desired interacting clone in the AD library, we have screened about $2 \times 10^6$ clones.

We have performed five transformations and the results of all these transformations are outlined in the table below:

| | |
|---|---|
| Total # of clones screened | $1.8 \times 10^6$ |
| Transforming efficiency (cells/μg of DNA) | $1 \times 10^4$ |
| Total # of clones obtained with only His3/selection | 250 |
| Total # of clones obtained after second screen with lacZ | 26 |

Figure 3A:
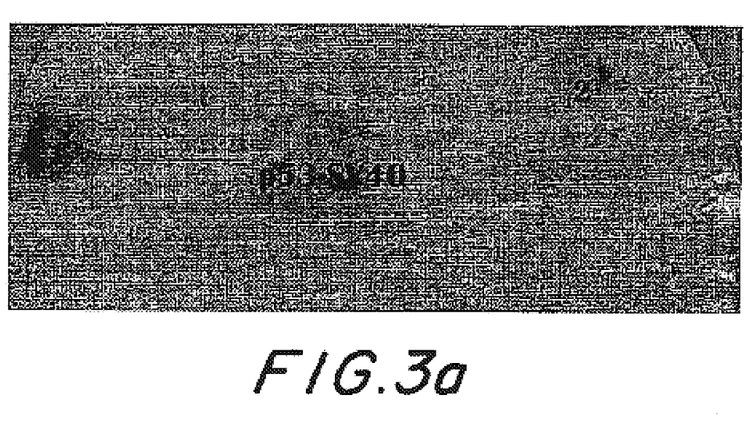
FIGS. 3a and 3b: Peptide library transformation. The yeast strain CG-1945 was transformed with 60 μg of library plasmids. The cells were grown on SD/-Trp/-Leu/-His/+10 mM 3-AT agar medium at 30° C. After 4 days, some $His^+$ colonies appeared on the plates. In the first transformation, we have isolated 20 $His^+$ clones; only 9 of them, numbered in the figure, were also $lacZ^+$.
Figure 3B:
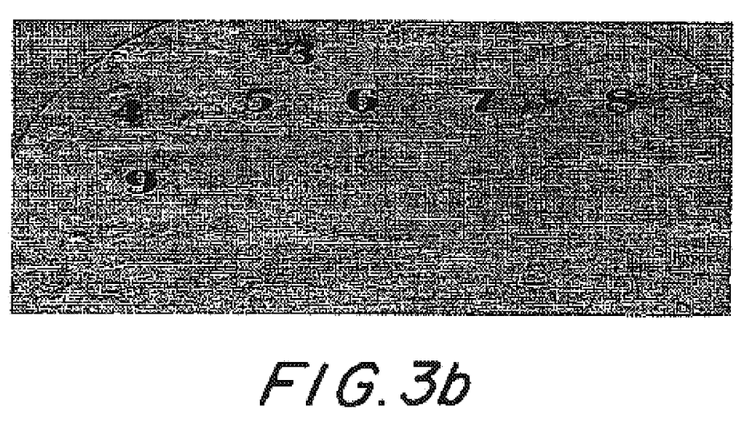

After selection for the histidine nutritional requirement (i.e. selection for THS interactions with the His3 reporter gene), a total of 250 clones did survive out of $1,8 \times 10^6$ transformed clones. Successively, by the screening for the second reporter gene lac-Z, we have found 26 yeast positive clones (FIG. 3).

Example 2

Isolation of True Positive Clones

In order to eliminate the great majority of residual false positives, the THS-selected plasmids coding for the peptide library have been back-transformed into the original screening strain, CG-1945, in the following conditions: 1) with no additional plasmid; 2) with a plasmid encoding the GAL4 DNA-binding domain alone (pAS2-1); 3) with the full "bait" plasmid or 4) with an unrelated fusion protein (like the human lamin-C fused to GAL4-BD) (Bartel et al., 1993).

A true positive clone produces a positive signal only in the third condition listed above.

In order to accomplish the above task, we have isolated to homogeneity positive "fish" plasmids and transformed them in E. coli. These AD/library plasmids have been selectively amplified in E. coli using its LEU2 marker to complement the E. coli leuB mutation of strain HB101.

Figure 4:
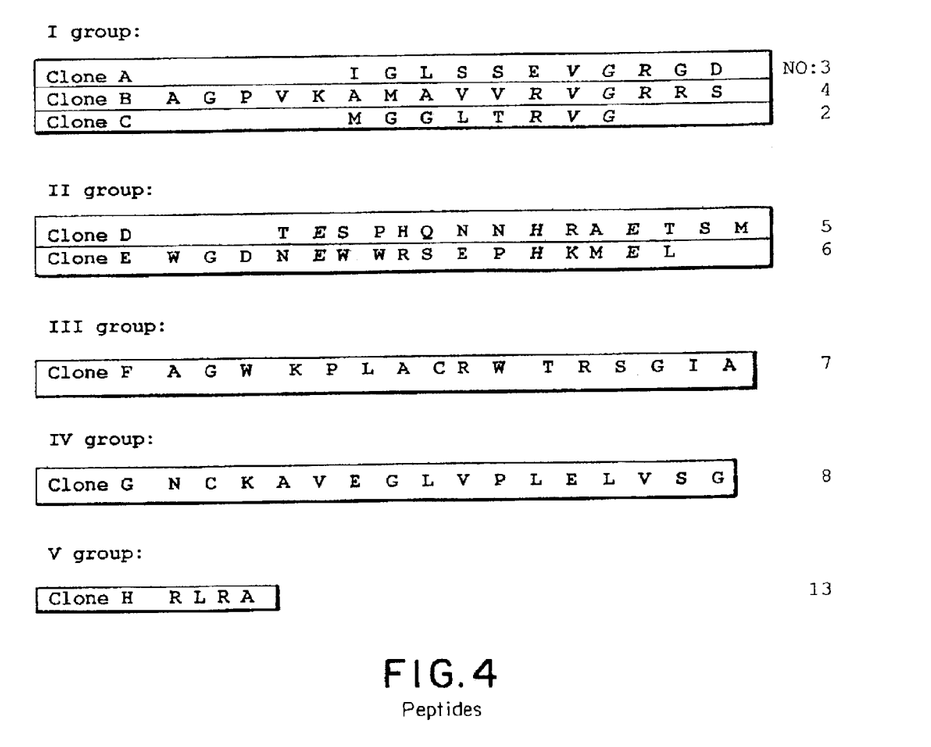
FIG. 4: Peptides. The peptides isolated by THS: they are assembled in five homology groups, where group I include Clone A (SEQ ID NO:3), Clone B (SEQ ID NO:4), and Clone C (SEQ ID NO:2); group II includes Clone D (SEQ ID NO:5), and Clone E (SEQ ID NO:6); group III includes Clone F (SEQ ID NO:7); group IV includes Clone G (SEQ ID NO:8); and group V includes Clone H (SEQ ID NO:13).

These plasmids have been used to back-transform yeast strain in order to eliminate false positives as described above: after these procedures, we selected nine positive clones (FIG. 4).

The data obtained from the sequence analysis have indicated that (i) although all clones screened contain more than one $(NNK)_{16}$ (SEQ ID NO: 19) oligonucleotide, only the first oligonucleotide sequence is expressed as a GAL4 AD/peptide fusion due to the in-frame stop codon at the end of every oligonucleotide; (ii) most of the isolated peptides have the expected full length of 16 amino acids; (iii) some of the peptides presented homologies with known gp130-ICD interacting proteins.

In order to confirm gp130-ICD-peptide interaction, we have also switched cloning vectors by moving the library insert from the AD to the DNA-BD vector and vice-versa. Then we have repeated the THS assay (Van Aelst et al., 1993).

Figure 5:
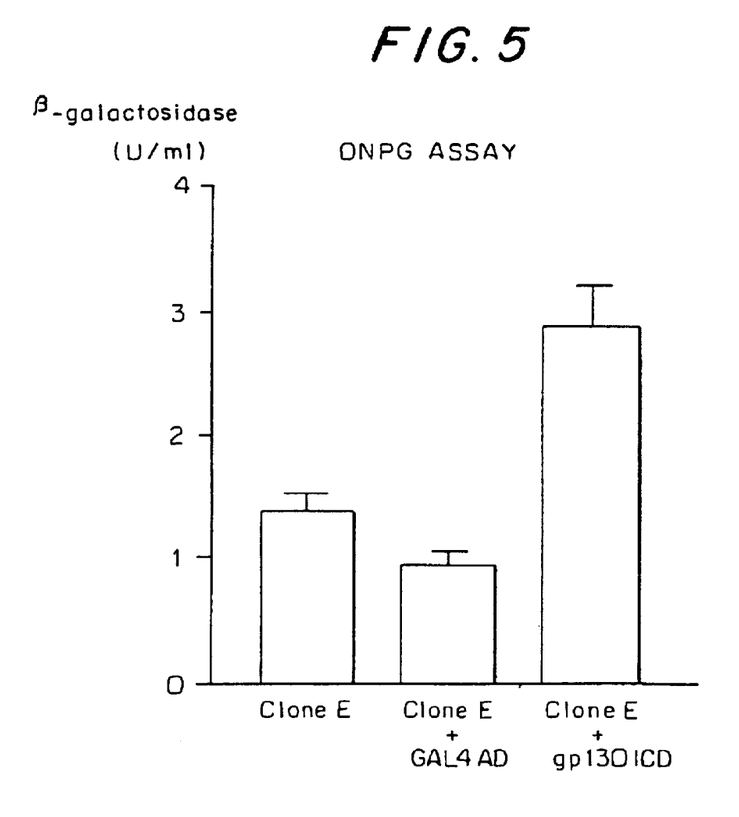
FIG. 5: β-galactosidase (LacZ) activity in liquid assay. The combination of clone E and gp130-ICD in yeast cells generated about 3 units/ml of LacZ activity. The value is obtained from three independent experiments.

We have also performed liquid β-galactosidase assays to quantify transcriptional activity: as shown in the FIG. 5, in the presence of gp130-ICD/GAL4AD the fusion protein clone E/GAL4BD was able to produce a transcriptional activity of lacZ gene about 2 to 3 fold higher than in the absence of gp130-ICD/GAL4AD, thus confirming the interaction detected after the first selection.

Homologies

Figure 6:
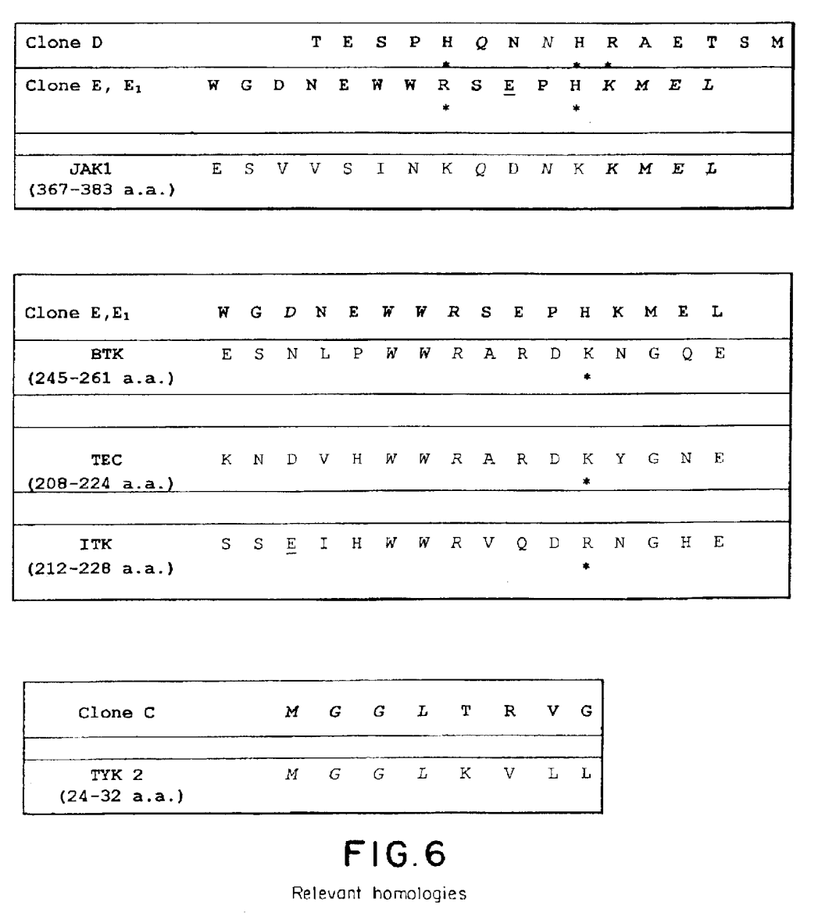
FIG. 6: Relevant homologies. Sequence alignment of the peptides D, E ($E_1$) and C with several gp130-associated tyrosine kinases, JAK1 (SEQ ID NO:14), BTK (SEQ ID NO:15), TEC (SEQ ID NO:16), ITK (SEQ ID NO:17), and TYK 2 (SEQ ID NO:18). Identities are indicated as italics; basic amino acids are marked as (*); acidic amino acids are underlined.

Protein databases search has proved to be very interesting, because it has revealed homologies between the isolated peptides and proteins like JAK1 and Tec which are constitutively associated with the intracytoplasmic domain of gp130. Even if these homologies are limited to small stretches, these results could be useful to direct our future investigations (FIG. 6). We have selected the clone E in two independent transformations: this clone shows an homology with JAK1. Harpur and co-workers have proposed that the JAK kinases be divided into seven domains designated JAK homologies (JH) domains 1 through 7 (Harpur et al., 1992).

JH1 corresponds to the tyrosine kinase domain and JH2 corresponds to the putative serine-threonine kinase domain. The domains JH3 trough JH7 are non-catalytic domains and have no know function. Clone E shows a little region of homology with JAK1: this homology falls in the JH4 domain.

Harpur and co-workers have suggested that the association of JAK2 with the GH receptor must be mediated by the non catalytic domains, JH3 through JH7: these domains are structurally and functionally conserved in members of the JAK family. JH4 is the most conserved among these domains. Therefore our data suggest that the stretch of JAK1 defined by peptide E might play a functional role: it could mimic JAK1 binding site on gp130. Also the clone C shows an interesting homology with Tyk2: this homology falls in the JH7.

The other clones show identities with other kinases like LTKR or with proteins like ANK1, whose functions include the attachment of integral membrane proteins to cytoskeletal elements.

Discussion

Studies of cytokine signaling pathways suggest that signals are generated by protein-protein interactions mediated by the association of small, modular protein domains with short and specific amino acid sequences. For example, Src homology 2 (SH2) and Src homology 3 (SH3) domains are regions of 60–100 amino acids that interact with phosphorylated tyrosine residues or proline-rich regions, respectively.

Therefore, it is conceivable that discrete domains of the JAK kinases or of the receptors are required for binding of the JAK kinases and in some cases they might determine the specificity of such binding.

Published data indicate the precise sites of gp130-ICD involved in some of these interactions: for example, the box1 domain of gp130 is an eight amino acid motif rich in proline residues. This domain should directly be involved in the interaction with the JAK kinases, also if it seems more probable that the box1 sequence plays a critical role in generating a secondary structure that is required for the interaction between JAK kinases and the cytokine receptors (Murakami et al., 1991). Another domain of gp130 involved in protein-protein interactions is the consensus sequence YXPQ involved in STAT3 and STAT1 activation (Gerhartz et al., 1996).

We have examined the association of gp130-ICD with a random peptide library by the THS. We have identified nine independent clones/peptides: these peptides show homologies with proteins present in data bank. Even if these homologies are limited to small stretches, these results could be useful to direct our future investigations.

If these preliminary data will be confirmed, we could identify the exact regions of kinases, such as JAK1, which bind to gp130-ICD. Our data might also suggest that a two-hybrid system peptide screening is a suitable technique to reach similar results.

Materials and Methods

Construction of Plasmids Encoding Hybrid Proteins

All the hybrid constructs were created using amplification by RT-PCR.

The PCR reactions contained 10 µl of cDNA of HepG2 cells, 50 pmoles of each primer (see below), 2.5 units of Stratagene Pfu polymerise, 0.2 mM of each of the four deoxynucleotide triphosphates, 10 µl of Pfu buffer, in a reaction volume of 100 µl, overlaid with 50 µl of mineral oil.

Amplification was performed for 30 cycles with a temperature profile of 45 seconds at 94° C., 45 seconds at 60° C. and 6 minutes at 72° C.

All of the PCR fragments were digested with appropriate restriction enzymes (EcoRI/BamHI for hgp130) overnight at 37° C.

The digested PCR products were purified by low melting agarose gel electrophoresis and by Microcon 100 (Amicon). These fragments were ligated with the Rapid DNA ligation kit (Boehringer Mannheim) into both the pAS2-1 and pGADGH vectors and transformed into E. coli Top10F' competent cells (Invitrogen).

The MATCHMAKER Random Peptide Library (Clontech) consists of synthetic (NNK)$_{16}$ (SEQ ID NO:19) oligonucleotides (N=A, G, C or T; K=T or G), flanked by BamHI and EcoRI sites and containing a terminal stop codon, directionally cloned in the high-expression GAL4 activation domain (AD) vector pGADGH. A mixture of random 16-codon peptides fused to the GAL4AD is generated from the vector.

PCR Primers

Upgp130:
(SEQ ID NO: 9)
5' CTG GAA TTC AAT AAG CGA GAC CTA ATT AAA AAA CAC ATC TGG CCT AAT GTT C 3'

Logp130:
(SEQ ID NO: 10)
5' ACA CGG GAT CCT CAC TGA GGC ATG TAG CCG CCT TGC CGT ACA GTC 3'

The human gp130-ICD cDNA was PCR amplified using Upgp130 and Logp130.

DNA Sequencing

DNA sequencing was performed on both strands using the DNA Sequencing Kit, Dye Primer Cycle Sequencing (Perkin Elmer, Applied Biosystems Division, Foster City, Calif., USA) on an ABI model 373A automated sequencer, following manufacturer instructions.

Homology search was performed against GenBank, EMBL and Swiss-Prot databases.

Sequencing Primers

Primer 1 (GAL4 BD):
5' TCA TCG GAA GAG TAG 3'    (SEQ ID NO: 11)

Primer 2 (GAL4AD):
5' TAC CAC TAC AATGGA TG 3'    (SEQ ID NO: 12)

E. coli Strains and Media

HB101: F⁻, hsdS20 (r⁻b, m⁻b), recA13, ara-14, pro A2, lacY1, galK2, rspL20 (Sm$_r$), xyl-5, mtl-1, supE44

Top10F': F', lacI$^q$, Tn10, Tet$^r$, mcrA Δ(mrr-hsdRMS-mcrBC) Φ80 lacZ ΔM15 ΔlacX74 deo R recA1 araD139 Δ(ara-leu)7697 galU galK rpsL endA1 nupG

| LB (1l): | 10 g Bactotryptone |
| --- | --- |
|  | 5 g Yeast extract |
|  | 10 g NaCl |
| LB agar (1l): | 10 g Bactotryptone |
|  | 5 g Yeast extract |
|  | 10 g NaCl |
|  | 1.5% agar |

Yeast Strain and Media

The Saccharomyces cerevisiae strain CG-1945 (Mat a, ura 3-52, his3-200, lys 2-801, ade 2-101, trp 1-901, leu2-3, 112, gal4-542, gal 80-538, cyh$^r$ 2, LYS::GAL1 $_{UASr}$-GAL1$_{TATA}$-HIS3, URA3::GAL4$_{17-mar(x3)}$-CyC1$_{TATA}$-lacZ) (Clontech Matchmaker) were used for all assays. CG-1945 carries two reporter genes under the control of different promoters: lacZ gene under the control of the CYC1 promoter, which has its own upstream activation sequence replaced with GAL4 binding sites, and His3 gene under the control of the Gal1 promoter.

Thus these promoters share little other than the GAL4 binding sites and the screening performed with both reporter genes in the same yeast cells should eliminate many false positives. Yeast cultures were grown at 30° C. in either YPD medium (1% yeast extract, 2% peptone and 2% glucose) or SD minimal medium (0.5% yeast nitrogen base without amino acids, 2% glucose, and 1% desired amino acid dropout solution).

Yeast Transformation and β-Galaclosidase Assay

Fusion genes were introduced into CG-1945 strain by the lithium acetate transformation procedure (16). We have spread all cells on SD/-Trp-Leu-His+3AT 10 mM agar medium for performing a first selection. When interaction occurs between gp130-ICD and a peptide, the two GAL4 functional domains are tethered, resulting in the histidine expression. Yeast cells with interacting hybrid proteins can thus grow in a medium lacking of this amino acid.

3-AT (3-amino1,2,4-triazole), a competitive inhibitor of the yeast HIS3 protein (imidazoleglycerol-phosphate dehydratase), is used to inhibit low levels of His3p leaky expressed in some reporter strains. Transformants were allowed to grow at 30° C., usually for 2–4 days, until colonies were large enough to assay for β-galactosidase activity.

Transformants were replicated on sterile Whatman number 1 filter that had been layered on selective growth media. After colonies had grown, we perform two or more freeze/thaw cycles, placing the filter in liquid nitrogen and at room temperature for 0.5–1 minute.

The filter was placed in 5 ml Z-buffer/X-gal solution in a clean 100-mm plate and incubated at 30° C. typically from 30 minutes to 8 hours. The filter was dried and photographed to record the data.

Mouse p53 protein and SV40 large T-antigen are known to interact in the THS.

The following plasmids, pVA3-1, which encodes the GAL4 DNA-binding domain-murine p53 hybrid, and pTD1-1, which encodes the GAL4 activation domain-SV40 large T-antigen hybrid, were used as a positive control in the β-galactosidase assay.

Liquid β-Galactosidase Assay

We prepared 5-ml overnight culture in liquid SD selection medium appropriate for plasmids.

We transferred 2 ml of the culture to 8 ml of YPD and incubate at 30° C. for 3–5 hours until the cells are in the mid-log phase (O.D.$_{600}$=0.5–0.8).

The culture was centrifuged at 14,000 rpm for 30 seconds: in the next step, we remove the supernatants, wash the cells with a volume of Z-buffer and resuspend the pellet in 900 μl of Z buffer.

Immediately, two or more freeze/thaw cycles were performed, placing the tubes in liquid nitrogen and in a 37° C. water bath for 0.5–1 minute. Finally, we added 0.7 ml of β-mercaptoethanol-Zbuffer solution and 160 μl of ONPG (o-nitrophenyl β-galactopyranoside, Sigma) 4 mg/ml dissolved in Z buffer to each tubes: the tubes were incubated at 30° C. until the yellow colour developed.

The reaction was stopped by adding 0.4 ml of 1 M Na$_2$CO$_3$: we recorded the time needed to obtain the results and O.D.$_{420}$ of the samples.

β-galactosidase units were calculated by this formula:

$$\beta\text{-galactosidase units} = 1,000 \times O.D._{420}/(t \times V \times O.D._{600})$$

Where: t=elapsed time in min of incubation; V=0.1 ml; O.D.$_{600}$=A$_{600}$ of 1 ml of culture.

Yeast Protein Extract and Western Blotting

For each transformed yeast strain, we prepared 5 ml overnight cultures in SD selection medium appropriate for our plasmids; also we prepare a 10 ml culture of the untransformed CG-1945 in YPD as a negative control. For each clone to be assayed (and the negative control) separately we transferred overnight cultures in 50 ml of appropriate medium.

We incubated the culture at 30° C. with shaking until the O.D.$_{600}$ reached 0.4–0.6: the culture was quickly chilled by pouring it into a pre-chilled 100 ml centrifuge tube and immediately centrifuged at 1000×g for 5 min at 4° C. We discarded supernatant and resuspended the cell pellet in 50 ml of ice-cold water: the pellet was recovered by centrifugation at 1,000×g for 5 min at 4° C. We resuspended cell pellet with Cracking buffer (Urea 8M, SDS 5%, Tris-HCl 40 mM, EDTA 0.1 mM, bromophenol blue, protease inhibitor solution); we added 80 μl of glass beads (425–600 μm, SIGMA). The samples were heated at 70° C. for 10 minutes and vortexed for 1 minute. Pellet debris and unbroken cells were spun in a microcentrifuge at 14,000 rpm for 5 minutes. The supernatants were transferred to fresh 1.5 ml screw-cap tubes and briefly boiled. Samples were immediately loaded onto a gel or stored at –70° C.

We performed Western blotting using soluble protein extracts from the transformants loading on 15% acrylamide gel. We probed the blots with GAL4 domain-specific monoclonal antibodies, such as the GAL4 BD and AD mAbs from Clontech. We used for detection a secondary antibody HRP-conjugated Goat anti-mouse IgG (BIORAD).

REFERENCES

Bartel, P. L. et al., (1993) Elimination of false positives that arise in using the two-hybrid system. *BioTechniques* 14,920–924;

Brakenhoff, J. P. et al., (1995) Development of human IL-6 receptor antagonists. *Annals of the New York Academy of Sciences* 762, 129–34;

Darnell, J. E. et al. (1994). JAK-STAT pathways and transcriptional activation in response to IFNs and other extracellular signaling proteins. *Science* 264, 1415–1421;

Estojak J. et al., (1995). Correlation of two-hybrid affinity data with in vitro measurements. *Molecular and Cellular Biology* 15, 5820–5829;

Fields, S. et al., (1994). The two-hybrid system: an assay for protein-protein interactions. *Trends in Genetics* 10, 286–292;

Gerhartz, C. et al., (1996) Differential activation of acute phase response factor/STAT3 and STAT1 via the cytoplasmic domain of the interleukin 6 signal transducer gp130 *Journal Biological Chemistry* 271, 12991–12998;

Gietz, D. et al., (1992) Improved method for high efficiency transformation of intact yeast cells. *Nucleic Acid Res.* 20, 1425;

Harpur, A. G. et al., (1992) JAK2, a third member of the JAK family of protein tyrosine kinases. *Oncogene* 7, 1347–1353;

Hirano T. et al., (1994) Stem Cells, 12, 262–277;

Kallen, K. J. et al., (1997) The therapeutic potential of interleukin 6 hyperagonists and antagonists. *Expert Opin. Invest. Drugs* 6, 237–266;

Lütticken, C. et al., (1993) Association of transcription factor APRF and protein kinase JAK1 with the interleukin-6 signal transducer gp130. *Science* 263, 89–92;

Matsuda, T. et al., (1995) Association and activation of Btk and Tec tyrosine kinases by gp130, a signal transducer of the interleukin-6 family of cytokines. *BLOOD* 85, 627–633;

Murakami, N. et al., (1991) Critical cytoplasmic region of the interleukin 6 signal transducer gp130 is conserved in the cytokine receptor superfamily *Proc. Nat. Acad. Sci. USA* 88, 11349–11353;

Tanner, J. W. et al., (1995) The conserved box1 motif of cytokine receptors is required for association with JAK kinases. *Journal of Biological Chemistry* 270, 6523–6530;

Van Aelst, L. et al., (1993). Complex formation between RAS and RAF and other protein kinases. *Proc. Nat. Acad. Sci. USA* 90, 6213–6217;

VanderKuur, J. A. et al., (1994) Domains of the growth hormone receptor required for association and activation of JAK2 tyrosine kinase. *Journal Biological Chemistry* 269, 21709–21717;

Yamasaki et al., *Science,* 241, 825–828, 1988;

Yang M. et al., (1995) Protein-peptide interactions analyzed with the yeast two-hybrid system. *Nucleic Acids Research* 23, 1152–1156;

---

What is claimed is:

1. An IL-6 antagonist peptide, isolatable from a peptide library by binding to the intracellular domain of gp130 in a two-hybrid system for detecting protein-protein interaction, said peptide comprising SEQ ID NO:6, as well as salts, functional derivatives, and conservatively substituted analogs thereof having IL-6 antagonist activity.

2. The peptide according to claim 1, comprising the amino acid sequence of SEQ ID NO:6.

3. The peptide according to claim 1, consisting of the amino acid sequence of SEQ ID NO:6, as well as salts, functional derivatives, and conservatively substituted analogs thereof having IL-6 antagonist activity.

4. The peptide of claim 3, wherein said conservatively substituted analogs consist of one or two conservatively substituted amino acid residues in SEQ ID NO:6.

5. The peptide of claim 1, wherein said conservatively substituted analogs consist of one or two conservatively substituted amino acid residues in SEQ ID NO:6.

6. A pharmaceutical composition comprising the peptide of claim 1 and a pharmaceutically acceptable carrier or excipient.

7. A composition, comprising the peptide of claim 1 and a pharmaceutically-acceptable carrier or excipient.

* * * * *

SEQUENCE LISTING

```
<160> NUMBER OF SEQ ID NOS: 19

<210> SEQ ID NO 1
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(4)
<223> OTHER INFORMATION: Xaa is selected among Gly, Leu and Ser
<220> FEATURE:
<221> NAME/KEY: misc_feature
<222> LOCATION: (9)..(12)
<223> OTHER INFORMATION: Xaa, if any, is selected among Gly, Arg, Asp
      and Ser

<400> SEQUENCE: 1

Met Gly Xaa Xaa Thr Arg Val Gly Xaa Xaa Xaa Xaa
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Met Gly Gly Leu Thr Arg Val Gly
1               5

<210> SEQ ID NO 3
<211> LENGTH: 11
<212> TYPE: PRT
<213> ORGANISM: Artificial Sequence
<220> FEATURE:
<223> OTHER INFORMATION: synthetic

<400> SEQUENCE: 3

Ile Gly Leu Ser Ser Glu Val Gly Arg Gly Asp
1               5                   10

<210> SEQ ID NO 4
<211> LENGTH: 16
<212> TYPE: PRT
<213> ORGANISM: Artificial Sequence
<220> FEATURE:
<223> OTHER INFORMATION: synthetic

<400> SEQUENCE: 4

Ala Gly Pro Val Lys Ala Met Ala Val Val Arg Val Gly Arg Arg Ser
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic
```

```
<400> SEQUENCE: 5

Thr Glu Ser Pro His Gln Asn Asn His Arg Ala Glu Thr Ser Met
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic

<400> SEQUENCE: 6

Trp Gly Asp Asn Glu Trp Trp Arg Ser Glu Pro His Lys Met Glu Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetic

<400> SEQUENCE: 7

Ala Gly Trp Lys Pro Leu Ala Cys Arg Trp Thr Arg Ser Gly Ile Ala
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Asn Cys Lys Ala Val Glu Gly Leu Val Pro Leu Glu Leu Val Ser Gly
1               5                   10                  15

<210> SEQ ID NO 9
<211> LENGTH: 52
<212> TYPE: DNA
<213> ORGANISM: Artificial Sequence
<220> FEATURE:
<223> OTHER INFORMATION: synthetic

<400> SEQUENCE: 9
ctggaattca ataagcgaga cctaattaaa aaacacatct ggcctaatgt tc          52

<210> SEQ ID NO 10
<211> LENGTH: 45
<212> TYPE: DNA
<213> ORGANISM: Artificial Sequence
<220> FEATURE:
<223> OTHER INFORMATION: synthetic

<400> SEQUENCE: 10
acacgggatc ctcactgagg catgtagccg ccttgccgta cagtc                  45

<210> SEQ ID NO 11
<211> LENGTH: 15
<212> TYPE: DNA
<213> ORGANISM: Artificial Sequence
<220> FEATURE:
<223> OTHER INFORMATION: synthetic

<400> SEQUENCE: 11
tcatcggaag agtag                                                   15
```

```
<210> SEQ ID NO 12
<211> LENGTH: 17
<212> TYPE: DNA
<213> ORGANISM: Artificial Sequence
<220> FEATURE:
<223> OTHER INFORMATION: synthetic

<400> SEQUENCE: 12
taccactaca atggatg                                                   17

<210> SEQ ID NO 13
<211> LENGTH: 4
<212> TYPE: PRT
<213> ORGANISM: Artificial Sequence
<220> FEATURE:
<223> OTHER INFORMATION: synthetic

<400> SEQUENCE: 13

Arg Leu Arg Ala

<210> SEQ ID NO 14
<211> LENGTH: 16
<212> TYPE: PRT
<213> ORGANISM: Artificial Sequence
<220> FEATURE:
<223> OTHER INFORMATION: synthetic

<400> SEQUENCE: 14

Glu Ser Val Val Ser Ile Asn Lys Gln Asp Asn Lys Lys Met Glu Leu
1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic

<400> SEQUENCE: 15

Glu Ser Asn Leu Pro Trp Trp Arg Ala Arg Asp Lys Asn Gly Gln Glu
1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic

<400> SEQUENCE: 16

Lys Asn Asp Val His Trp Trp Arg Ala Arg Asp Lys Tyr Gly Asn Glu
1               5                  10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic

<400> SEQUENCE: 17

Ser Ser Glu Ile His Trp Trp Arg Val Gln Asp Arg Asn Gly His Glu
1               5                  10                  15

<210> SEQ ID NO 18
```

-continued

```
<211> LENGTH: 8
<212> TYPE: PRT
<213> ORGANISM: Artificial Sequence
<220> FEATURE:
<223> OTHER INFORMATION: synthetic

<400> SEQUENCE: 18

Met Gly Gly Leu Lys Val Leu Leu
1               5

<210> SEQ ID NO 19
<211> LENGTH: 48
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(48)
<223> OTHER INFORMATION: "n" at each occurrence is a, g, c or t
<220> FEATURE:
<221> NAME/KEY: misc_feature
<223> OTHER INFORMATION: "k" at each occurrence is t or g

<400> SEQUENCE: 19
nnknnknnkn nknnknnknn knnknnknnk nnknnknnkn nknnknnk              48
```